United States Patent [19]

Hennequin et al.

[11] Patent Number: 4,944,755
[45] Date of Patent: Jul. 31, 1990

[54] MOTORIZED JOINT

[75] Inventors: James R. Hennequin, Bedford; Peter Fluck, Cambridge, both of United Kingdom

[73] Assignee: Air Muscle Limited, Kepston Bedford, United Kingdom

[21] Appl. No.: 213,701

[22] PCT Filed: Oct. 21, 1987

[86] PCT No.: PCT/GB87/00743
§ 371 Date: Jun. 20, 1988
§ 102(e) Date: Jun. 20, 1988

[87] PCT Pub. No.: WO88/03008
PCT Pub. Date: May 5, 1988

[30] Foreign Application Priority Data

Oct. 21, 1986 [GB] United Kingdom ............... 8625144

[51] Int. Cl.$^5$ .................................................. A61F 2/30
[52] U.S. Cl. .................................. 623/19; 623/18; 623/26; 128/26; 901/21; 901/28
[58] Field of Search .................. 623/24, 25, 26, 39, 623/59, 61, 62, 19, 18; 128/26; 901/21, 28

[56] References Cited

U.S. PATENT DOCUMENTS

| 3,343,864 | 9/1964 | Baer | 623/26 X |
| 3,937,215 | 2/1976 | Barthlome | 128/26 |
| 4,274,399 | 6/1981 | Mummert | 128/26 |
| 4,393,728 | 7/1983 | Larson | 901/27 X |
| 4,671,258 | 6/1987 | Barthlome | 128/26 |
| 4,739,692 | 4/1988 | Wassam et al. | 901/21 X |
| 4,867,140 | 9/1989 | Hovis et al. | 128/24 R |

FOREIGN PATENT DOCUMENTS

| 0828291 | 1/1952 | Fed. Rep. of Germany | 623/26 |
| 1229027 | 5/1986 | U.S.S.R. | 901/21 |
| 1286821 | 8/1972 | United Kingdom . | |

Primary Examiner—Richard J. Apley
Assistant Examiner—Joe H. Cheng
Attorney, Agent, or Firm—Fitch, Even, Tabin, Flannery

[57] ABSTRACT

The invention provides a motorized joint which has a pair of members that are movable relative to one another about a joint. Power to actuate the joint is provided by an inflatable hose inflating to transmit the force due to the expansion thereof via a strap or other elements interconnecting the members. The motorized joint can be covered with artificial flesh which, together with the expansion of the inflatable hose, creates the realistic appearance of a muscle flexing.

10 Claims, 5 Drawing Sheets

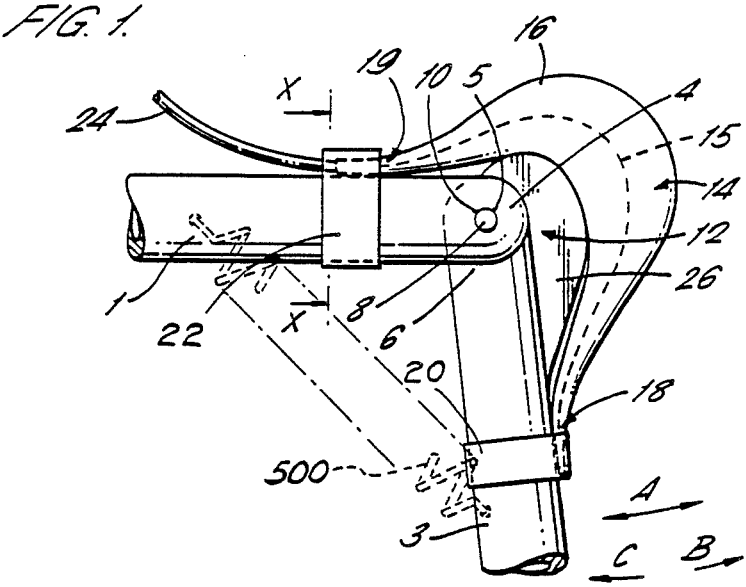
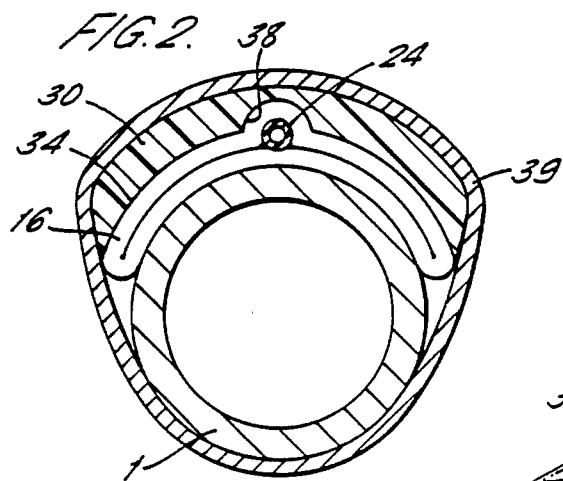
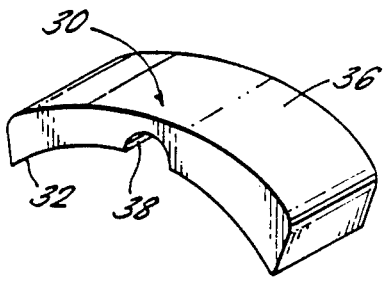

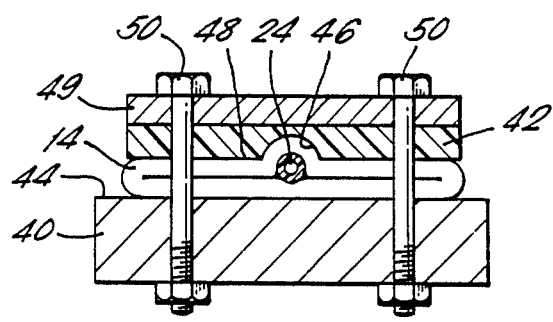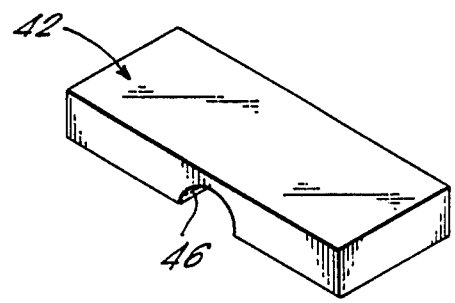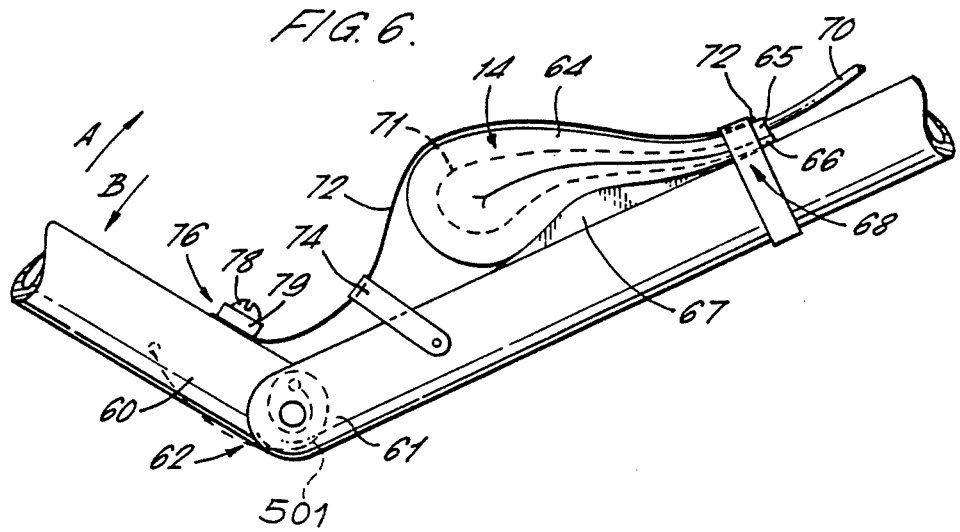

MOTORIZED JOINT

The present invention relates to a motorized joint for producing the realistic appearance and action of animal or human muscles in artificial limbs.

Artificial limbs are commonly prepared for amputees and people having comparable disabilities. Unfortunately, such limbs are rarely attractive, and fail to reproduce the appearance of the limbs they are intended to replace. This can have adverse psychological effects on the wearers of the limbs.

Additionally, the limbs are increasingly required as constituent parts of experimental and industrial robots, and there is a growing range of applications of artificial limbs in high technology animated television and cinema productions. Further, successful television and film recordings encourage secondary markets in the merchandising of souvenir models of characters appearing in such productions. It has been a long standing problem that, in order to manufacture the souvenir models sufficiently cheaply to exploit the intended market for them, the models do not accurately reproduce the appearance or actions of the characters upon which they are based.

Accordingly, the present invention provides A motorized joint in a skeleton structure comprising a pair of relatively movable limbs, an inflatable element having an inextensible wall acting between the limbs, means to interconnect the inflatable element to the limbs such that in one position of relative movement of the limbs the element is in a deflated, flat and folded condition and means to inflate the element causing the element to increase in cross-section and unfold to cause relative movement between the limbs from said one position to a further position of relative movement.

Such a motorized joint as defined above is characterized by a lack of internal inertia. This is brought about by the low level of internal friction in the motorized joint which may be pneumatically or hydraulically controlled. Thus, the problems, evident in previous joints, associated with the transition from static to dynamic friction (which is known as "break out" in the art) are absent from motorized joints according to the present invention. This solves a problem with previous artificial limbs that the movement of the limb is unnatural in appearance due to jerking of the joint as the inertia of previous motorized actuators is overcome. The movement of a motorized joint of the present invention is, by contrast, smooth and progressive and can be accurately controlled by a proportional controller, again enhancing the life-like nature of the movement of the muscle.

Further, a skeletal structure comprising a motorized joint according to the invention and a plurality of interconnected, further elements will have a realistic animal-like motion, since movement in one part of the skeleton will result in corresponding reactions elsewhere in the structure due to the interconnection of the elements thereof.

A further advantage of using an inflatable element to apply the force required to move the relatively movable limbs, which represent or replace the bones of the limb under consideration, is that the expansion of the inflatable element which accompanies the operation of the joint reproduces the action of an animal or human muscle, which enlarges when the muscle is flexed. Additionally, a motorized joint which incorporates an inflatable element to produce an actuating force requires fewer precision-manufactured components than previous artificial joints, and consequently is cheaper to manufacture and maintain than such previous designs. Such a joint is also quiet in operation.

Preferably, the relatively movable limbs are interconnected by a hinged joint. This feature permits the use of the motorized joint of the invention in artificial limbs designed to reproduce the appearance and function of actual animal and human joints.

Alternatively, the present invention provides a motorized joint in a skeleton structure comprising a pair of relatively movable limbs, an inflatable element having an inextensible wall acting between the limbs, means to interconnect the inflatable element to the limbs such that in one position of relative movement of the limbs the element is in a deflated, flat and folded condition and means to inflate the element causing the element to increase in cross-section and to unfold to cause relative movement between the limbs from said one position to a further position of relative movement, wherein the relatively movable limbs are interconnected by a framework. The advantage of this arrangement is that, in certain cases in human and animal skeletons, a complicated array of bones exists to effect a particular movement, such as rotation of the human arm about the shoulder joint. The use of a framework to locate the relatively movable limbs of the powered joint of the invention permits a reduction of the number of relatively movable components required to create the movement, and consequently simplifies the design of the joint.

Instead of the arrangements defined above, the present invention provides a motorized joint in a skeleton structure comprising a pair of relatively movable limbs, an inflatable element having an inextensible wall acting between the limbs, means to interconnect the inflatable element to the limbs such that in one position of relative movement of the limbs the element is in a deflated, flat and folded condition and means to inflate the element causing the element to increase in cross-section and to unfold to cause relative movement between the limbs from said one position to a further position of relative movement, wherein the relatively movable limbs are interconnected by a joint permitting relative rotation between said members.

Preferably, the inflatable element in any of the arrangements defined hereinabove acts directly between the relatively movable limbs.

Conveniently, the inflatable element comprises a length of inflatable, hollow hose sealed at one end thereof and having a generally flat transverse cross-section when in a deflated, unfolded state.

Further, it is preferable that the inflatable hose comprises means separating the opposing inner faces of said hose at the fold therein, thereby permitting passage of fluid between the two portions of the hose respectively on either side of said fold. Conveniently, the means separating the opposing inner faces of the hose comprises a length of flat, flexible, moulded plastic netting of narrower width than the interior transverse dimension of said hose, said netting being inserted lengthwise in said hose to maintain separation of the opposing faces of said hose on folding thereof.

Preferably the means to supply fluid under pressure to the inflatable element comprises a fluid supply pipe retained in the aperture at the open end of the inflatable hose, at least one sealing block adapted seal said end of the inflatable hose having the fluid supply pipe retained therein, clamping means to press said sealing block into contact with said end of the hose against a reaction surface also adapted to accommodate said end of the hose, pressurized fluid supply means selectively connectable to said supply pipe to supply inflating fluid thereto, and venting means selectively connectable to said supply pipe for use in deflating said inflatable hose.

According to a further preferred aspect of the present invention, the means to interconnect the inflatable element to the relatively movable limbs comprises clamping means securing the inflatable element to at least one of said relatively movable limbs.

Preferably, the means to interconnect the inflatable element to the relatively movable limbs comprises clamping means securing the inflatable element respectively to each relatively movable limb.

Alternatively, it is preferable that the means to interconnect the inflatable element to the relatively movable limbs comprises a flexible strap secured at each end thereof respectively to a relatively movable limb, the inflatable element being so disposed that, on inflation thereof, the force created in said inflatable element bears against said flexible strap, thereby creating tension in said flexible strap and occasioning movement between the relatively movable limbs.

A further preferable aspect of the invention is that the means interconnecting the inflatable element to the relatively movable limbs comprises a bearing surface disposed on one of said limbs, against which bearing surface the force created on inflation and deflation of the inflatable element reacts to magnify the relative movement of the limbs for a given inflation of said inflatable element.

Preferably, the motorized joint of the invention further comprises spring means interconnecting the relatively movable limbs which spring means, on deflation of the inflatable element, cause reversal of the movement between the relatively movable members.

In accordance with a preferable aspect of the invention, there is provided a motorized joint as defined hereinabove comprising artificial flesh surrounding said joint such that the joint resembles an animal joint and reproduces the appearance of the flexing of an animal muscle on inflation of the inflatable element.

Preferably, the motorized joint as defined herein comprises a plurality of pivotal axes and a corresponding plurality of inflatable elements.

In one aspect, the invention provides a skeletal structure having a multiplicity of motorized joints each as defined herein, wherein each joint comprises a corresponding multiplicity of inflatable elements.

According to yet a further preferable aspect of the invention, there is provided a pneumatic circuit comprising a plurality of motorized joints each as defined hereinabove.

In yet a further preferable aspect of the invention, there is provided a hydraulic circuit comprising a plurality motorized joints each as defined hereinabove.

There now follows a description of a number of specific embodiments of the invention, reference being made to the accompanying drawings in which:

FIG. 1 is a side elevational view of a motorized joint comprising a first preferred embodiment of the invention;

FIG. 2 is a cross-sectional view of apparatus according to the present invention for permitting inflation of an inflatable element thereof;

FIG. 3 is a perspective view of a sealing block for use in the apparatus of FIG. 2;

FIG. 4 is a cross-sectional view of apparatus to be used as an alternative to that shown in FIG. 2;

FIG. 5 is a perspective view of a sealing block for use in the apparatus of FIG. 4;

FIG. 6 is a side elevational view of a motorized joint comprising a second preferred embodiment of the invention;

Figure 7:
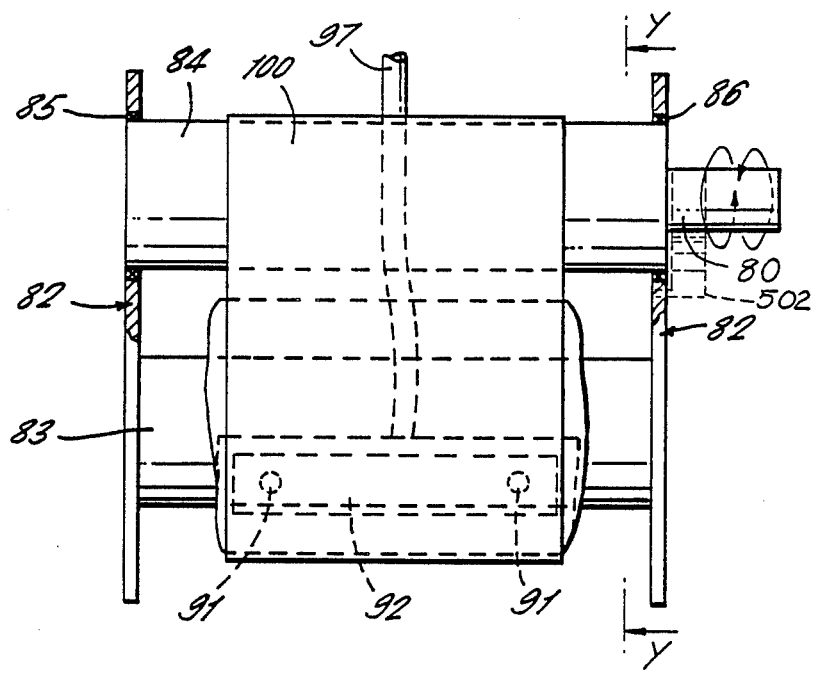
FIG. 7 is a front elevational view of a motorized joint comprising a third preferred embodiment of the invention.

Referring firstly to FIG. 1, there is shown a side elevational view of a simple motorized joint in an artificial limb in accordance with a first preferred embodiment of the invention.

The motorized joint comprises a first skeletal limb 1 of hollow, generally circular transverse cross-section hingedly connected by a pin joint to be described below to a second skeletal limb 3, which is also of hollow, generally circular transverse cross section. In the region of the pin joint, the cross sections of skeletal limbs 1, 3 are adapted to accommodate the pin joint. In the region referred to, skeletal limb 1 comprises two flattened forward-protruding lugs of which only one, indicated at 4 in FIG. 1, is visible in FIG. 1. Flattened lugs 4 are respectively disposed parallel to one another on opposite sides of the circumference of cylindrical limb 1 and have generally parallel inner faces. A through-bore 5 on a respectively common axis 8 passes through both lugs 4. Lugs 4 lie spaced apart from one another in the direction of the common axis. In the region of pin joint 12, second skeletal limb 3 comprises a single, flattened, forwardly protruding lug 6 disposed generally diametrically across the circular cross section of second skeletal limb 3 and having a through-bore on an axis common with axis 8 passing through lugs 4 referred to above. The width of lug 6 measured in the direction of axis 8 is smaller than the distance separating the parallel lugs 4. Lug 6 is disposed to lie in the axial space between the lugs 4. A pin 10 fixed at either end respectively to the lugs at the outer ends of the through-bore 5 therethrough passes through the through-bore in lug 6 referred to above. Pin 10 is a loose fit in the through-bore in lug 6, and thereby serves to locate lug 6 and skeletal limb 3 such that skeletal limbs 1 and 3 are rotatable relative to one another about axis 8 as indicated by the arrow A in FIG. 1. Thus the joint interconnecting skeletal limbs 1 and 3 in FIG. 1 is a movable pin joint, referred to generally at 12.

Interconnecting skeletal limbs 1 and 3 about the obtuse angle formed in the pin joint 12 is an inflatable element 14 formed as an inflatable hose 16. Inflatable hose 16 is secured at one end 18 to skeletal limb 3 by clamping means 20 to be described below and at the opposite end 19 thereof to skeletal member 1 by further clamping means 22.

The clamping means 20 secures the end 18 of inflatable hose 16 against movement relative to skeletal limb 3, and also seals the end 18 in an air-tight closure.

Clamping means 22 secures the end 19 of inflatable hose 16 against movement relative to skeletal limb 1 and also secures air supply and vent pipe 24, in a manner to be described below. Air supply and vent pipe 24 communicates with the interior of inflatable hose 16 and is retained in an air-tight joint such that pipe 24 is the only passage through which air may enter and leave inflatable hose 16. Air supply and vent pipe 24 is selectively connectable to a pressurized air supply source and a deflating vent arrangement respectively. In practice, the air supply source and vent are selectively connected to air supply pipe 24 by a multi-port solenoid operated control valve or similar means, which valve may be controllable by a hydraulic or pneumatic circuit, by manual operation or by computer.

Skeletal limb 3 comprises a moulded bearing pad 26 which may be of a suitable, hard plastic and which is formed as or rigidly secured to an upper portion of the member 3 such that inflatable hose 16 bears against the surface of bearing pad 26. In use, to operate the motor driven joint, air supply pipe 24 is connected to a pressurized air supply source (not shown) which therefore inflates hose 16 with pressurized air. As hose 16 inflates it tends to shorten the distance between the ends 18, 19 thereof and consequently operate joint 12 in the direction of arrow B by virtue of clamping means 20 and 22 transmitting the forces thus created in hose 16 to skeletal limbs 1 and 3 simultaneously. This effect is enhanced by the action of hose 16 against bearing pad 26 as the diameter of hose 16 increases on inflation, and is further enhanced by the fact that hose 16 is initially manufactured as a straight tube. When the artificial muscle is in a relaxed state, as is shown in FIG. 1, hose 16 is curved or folded about a transverse axis thereof. However, on inflation of hose 16 to activate the motor driven joint, hose 16 tends to return to the straight, as manufactured state thereof, and this effect enhances the effect of operating pin joint 12 in the direction of arrow B.

An effect which accurately reproduces the flexing of an animal muscle is observed in the inflatable hose 16 on inflation thereof, since the expansion of the hose 16 resembles that of an animal muscle during tensing or flexing thereof.

The motor driven joint of FIG. 1 may be operated in reverse by connecting air supply and vent pipe 24 to air vent means (not shown) again in practice by use of solenoid actuated control valves or similar means. This causes inflatable hose 16 to deflate on venting thereof, thereby causing hose 16 to revert to the deflated configuration described above. This deflating of hose 16 induces in the clamping means 20, 22 securing the ends 18, 19 respectively of inflatable hose 16 forces which act in generally the opposite directions to those incurred during inflation of the inflatable hose 16 and consequently cause the motorized joint to operate in the sense indicated by arrow C in FIG. 1.

However, it has been found that, while the forces referred to as acting on deflation of inflatable hose 16 are sufficient to operate the motorized joint of FIG. 1 in the direction of arrow C, such forces as are produced are not as great as those which act on inflation of inflatable hose 16. Thus, in particular situations including those where the motorized joint of FIG. 1 is to be included in a limb prosthesis for a disabled person, it may be necessary for the embodiment of the invention, shown in FIG. 1 to include a return spring 500 or similar device interconnecting the skeletal limbs 1, 3 across the acute angle formed therebetween. In such a case, inflation of inflatable hose 16 will always take place against the influence of the spring and consequently higher fluid pressures may be required for operation of the motorized joint. The return spring 500 may be in the form of a tension spring, elasticized members or the like.

Referring now to FIGS. 2 and 3 of the drawings there is shown an arrangement for clamping the inflatable element 14 of FIG. 1 to a skeletal limb while simultaneously sealingly retaining in an aperture thereof the fluid supply pipe 24 of FIG. 1. The arrangement of FIGS. 2 and 3 is therefore suitable for performing the function of the clamping means 22 shown in FIG. 1.

FIG. 2 is a cross-sectional view of a portion of limb 1 of FIG. 1 along lines X—X showing the region of the limb where inflatable hose 16 is secured to limb 1.

Limb 1 is shown as a hollow circular member secured to which is hose 16 having supply and vent pipe 24 inserted therein. Supply and vent pipe 24 is retained in the open end of hose 16 as shown by an adhesive compound. The adhesive compound serves to prevent the supply and vent pipe 24 from falling out of inflatable hose 16 during assembly of the motor driven joint. Disposed above inflatable hose 16 as shown in FIG. 2 is sealing block 30 which is shown in perspective view in FIG. 3. Sealing block 30 is generally curved in a transverse axial direction to enable a close fit between the inner surface 32 thereof and the upper surface 34 of inflatable hose 16 at the point of securing of the hose. Outer surface 36 of sealing block 30 is of generally similar curvature to that of inner surface 32. A longitudinally axial channel 38 of semi-circular cross section extends along the length of the inner surface 32 of sealing block 30. When sealing block 30 is positioned on inflatable hose 16, channel 38 mates with a raised portion in the upper surface 34 of inflatable hose 16 which raised portion is caused by the presence of supply and vent pipe 24 retained in the open end of hose 16 causing a bulge in the upper surface 34 thereof.

In use, sealing block 30 is forced down onto hose 16 against skeletal limb 1 by a clamping clip 39 which passes around sealing block 30 and limb 1 enclosing block 30, limb 1, hose 16 and pipe 24 within the circumference thereof. Clamping clip 39 applies a significant force to sealing block 30 with the effects of sealing the open end of hose 16 about supply and vent pipe 24 against fluid flow; enhancing the retention of pipe 24 within the end of hose 16; and securing inflatable hose 16 against movement relative to skeletal limb 1.

Clamping clip 39 may conveniently comprise a worm-drive hose clip.

An alternative to the arrangement shown in FIGS. 2 and 3 is depicted in FIGS. 4 and 5, which depict an arrangement for securing an inflatable element 14 in accordance with the invention to a skeletal limb 40 of generally flat surface contour.

FIG. 4 represents a comparable view of skeletal limb 40 to that shown of limb 1 in FIG. 2. Inflatable element 14 has an open end in which supply and vent pipe 24 is retained. Inflatable element 14 is secured to limb 40 and sealed around pipe 24 and at the open end thereof by the action of sealing block 42 pressing the end of inflatable member 14 against the upper surface 44, as shown in FIG. 4, of limb 40. Sealing block 42, as shown in FIG.

5, is of generally rectangular prismatic form having a channel 46 of generally semi-circular cross section formed therein. As in the arrangement shown in FIGS. 2 and 3, the semi-circular channel 46 mates with the bulge formed in the upper surface 48 of inflatable element 14 by the retention of pipe 24 within the open end of element 14. Sealing block 42 is pressed into contact with inflatable element 14 by shim 49 which in turn is clamped against sealing block 42 by nut and bolt assemblies 50 which secure the sealing arrangement to limb 40.

It will be clear that the sealing arrangements described above and illustrated in FIGS. 2 to 5 inclusive may be used for securing and sealing the ends of inflatable elements of the invention from which supply and vent pipes 24 are absent. In such cases, the sealing blocks 30 and 42 are not provided with semi-circular channels 38 and 46 respectively. It is necessary to seal inflatable elements 14 not having supply and vent pipes 24 when the inflatable element has been formed as a length of inflatable hose. In the embodiment of the invention described hereinabove, and in further embodiments to be described below, it is necessary both to secure and seal the opposite end of an inflatable hose to that having a supply and vent pipe retained therein. In such cases, such sealing blocks not having semi-circular channels are employed.

Folded inflatable hose 16 has inserted therein along the length thereof and around the fold a flat, flexible sheet of nylon mesh netting 15, such as the proprietary product "NETLON", which name is believed to be a Registered Trade Mark. The purpose of having a sheet of "NETLON" (shown by dotted lines in FIG. 1) inserted in particular about the fold in hose 16 is to ensure that, on inflation of hose 16, the opposing interior faces of the hose 16 at the point of folding do not seal the hose across the fold. This feature prevents a pocket of air from becoming trapped in a portion of hose 16 on deflation thereof.

Turning now to FIG. 6, there is shown a second preferred embodiment of the present invention comprising a pair of relatively movable, hollow, circular skeletal limbs 60, 61 interconnected by a movable pin joint 62 similar to pin joint 12 shown in FIG. 1.

Inflatable element 14 is an inflatable hose 64 which is doubled back upon itself to lie as a folded hose on bearing pad 67 of limb 61. Both ends 65, 66 of inflatable hose 64 are both sealed and clamped to limb 61 by a single clamping arrangement 68 which is similar to that described with reference to FIGS. 2 and 3 above. End 65 of inflatable hose 64 has retained and sealingly clamped therein a fluid supply and vent pipe 70 which is selectively connectable either to a source of pressurized air or a venting arrangement.

A flexible, inextensible strap 72 is secured at one end thereof in clamping arrangement 68 and extends from clamping arrangement 68 along the upper folded portion, as shown in FIG. 6, of inflatable hose 64. At the point on folded inflatable hose 64 where the curvature thereof becomes too great, due to the folding, for flexible strap 72 to remain in contact with the surface of the hose 64, flexible strap 72 breaks away from the surface of hose 64 and extends forwardly thereof to pass through hasp 74 and is firmly secured to skeletal limb 60 by further clamping means 76. Clamping means 76 comprises a screw and washer assembly, the screw 78 being screwed into skeletal limb 60 to cause washer 79 to grip flexible strap and prevent relative movement between the limb 60 and strap 72. Hasp 74 comprises a rigid or semi-rigid loop secured at a lower end thereof to limb 61, and through which loop flexible strap 72 passes as indicated above. In use, hasp 74 serves as a reaction member against which the tension to be created in flexible strap 72 reacts.

In use, the embodiment of the invention shown in FIG. 6 operates to move the skeletal limbs 60 and 61 in the sense of arrow A on inflation of folded, inflatable hose 64 and in the sense of arrow B on deflation of inflatable hose 64.

Inflation of inflatable hose 64 is occasioned by the selective connection, by virtue of solenoid operated pneumatic control valves, or similar means, of air supply and vent pipe 70 to a source of pressurized air (not shown). Air thus flows in to inflatable hose 64 and the effects of the expansion of hose 64; the reaction of hose 64 against strap 72 and the bearing surface 67 of limb 61; and the tendency of folded, inflatable hose 64 to unfold on inflation thereof combine to produce significant tension in flexible strap 72. The force in flexible strap 72 reacts at clamping arrangement 68, hasp 74 and clamping means 76 to cause relative axial movement of the limbs 60, 61 in the direction of arrow A in FIG. 6. The action of the motorized joint of FIG. 6 is broadly similar to that of FIG. 1.

On deflation of inflatable hose 64, deflation being caused by selective connection of supply and vent pipe 70 to a venting arrangement (not shown) the hose 64 reverts to the deflated state thereof as a folded hose lying along skeletal limb 61. The self-weight of skeletal members 60 and 61 acting during deflation against the resilience of flexible strap 72 is generally sufficient to cause relative movement of skeletal limbs 60 and 61 in the sense of arrow B in FIG. 6, but it may be necessary to provide a spring 501 to interconnect limbs 60 and 61 across the acute angle subtending therebetween and provide an additional return force in the powered joint.

Deflation of hose 64 is assisted, as in the embodiment of FIG. 1, by the presence of a sheet 71 of "NETLON" or similar material to prevent accidental sealing of the hose across the fold therein.

The embodiments of the invention described with reference to FIGS. 1 and 6 above are of particular use in the construction of motorized knee and elbow joints in artificial limbs for use in models, animated puppets and surgical prostheses.

Figure 8:
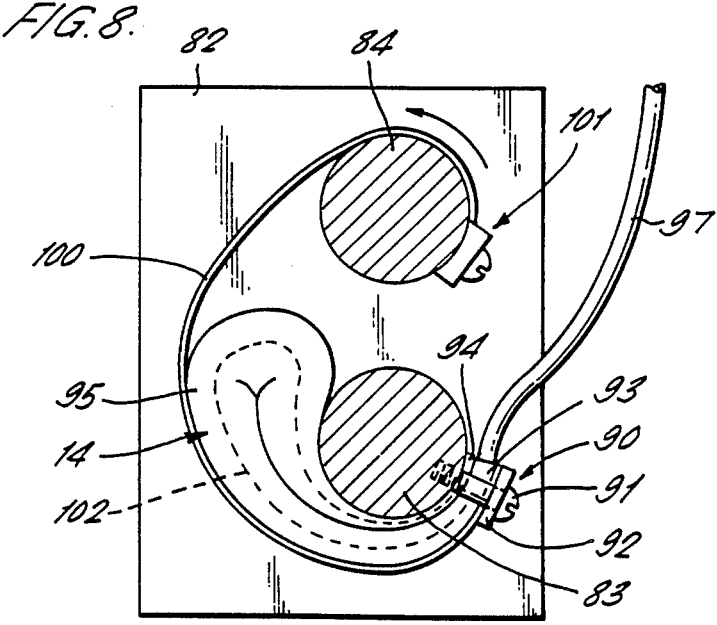
FIG. 8 is a cross-sectional view of the artificial joint of FIG. 7.

Referring now to FIGS. 7 and 8 there is shown a third preferred embodiment of the present invention.

This third embodiment of the invention is of use in the construction of motorized artificial shoulder and neck joints, and has applications in the fields of modelmaking and animated puppet manufacture.

FIG. 7 is a front elevational view of a motorized joint comprising an output shaft 80 which is to undergo controlled rotation in relation to a support framework 82 and fixed cylindrical skeletal limb 83. Output shaft 80 is formed as an axial extension of circular, skeletal limb 84 which is rotatable in bearings 85, 86 shown schematically in FIG. 7 disposed at, and supporting either end of rotatable limb 84. Bearings 85, 86 are mounted in frame members 82 which are interconnected by fixed limb 83, which limb is disposed to be generally parallel to rotatable limb 84.

Referring to FIG. 8, there is shown a cross-sectional view taken along the line Y—Y of FIG. 7, and showing the motor driven joint in greater detail.

A clamping arrangement 90 comprising screws 91 and a sealing block 92 of a type similar to that shown in FIG. 5 is shown in FIG. 8 at a point approximately 135° from the top dead center of fixed cylindrical limb 83 when measured in a clockwise sense. Sealing block 92 differs slightly from that shown in FIG. 5 since it is contoured to be a close fit on the surface of cylindrical, fixed limb 83.

Sealing block 92 is screwed into cylindrical fixed skeletal limb 83 at the position indicated and serves to clamp in position and seal both ends 93, 94 of an inflatable member 14 in the form of an inflatable hose 95 which is folded back on itself and is curved partially around limb 83 as shown in FIG. 8.

Sealing block 92 also secures air supply and vent pipe 97 to end 93 and which communicates with the interior of hose 95 and is selectively connectable to either a pressurized air supply source (not shown) or a venting arrangement for inflation and venting of the inflatable hose 95.

Sealing block 92 also serves to clamp flexible strap 100 at one end thereof. Flexible strap 100 extends of sealing block 92 about the outer surface contour of inflatable hose 95 as it lies about limb 83 and further extends forwardly thereof to contact the circumference of rotatable cylindrical limb 84 and follow said circumference to a point measured approximately, 135° clockwise rotation from the top dead center of limb 84 where the end of flexible strap 100 is clamped to limb 84 by a clamping arrangement 101 similar to those previously described.

Folded inflatable hose 95 has inserted therein along the length thereof and around the fold a flat, flexible sheet of nylon mesh netting 102, such as the proprietary product "NETLON", which name is believed to be a Registered Trade Mark. The purpose of having a sheet of "NETLON" (shown by dotted lines in FIG. 8) inserted in particular about the fold in hose 95 is to ensure that, on inflation of hose 95, the opposing interior faces of the hose 95 at the point of folding do not act to seal the hose across the fold. This has been found to be a significant defect of such hose not having a "NETLON" or similar insert to maintain a passage of air or other working fluid between the two portions of the hose on either side of the fold therein. On inflation of such inferior hose arrangements, a body of air becomes trapped in the portion of the hose on the far side of the fold from the air supply pipe and consequently complete deflation of the hose when required cannot take place.

In use the motorized joint of FIGS. 7 and 8 operates on selective connection of air supply and vent pipe 97 to a pressurized air supply (not shown) which supplies air under pressure to the interior of inflatable hose 95 having "NETLON" sheet 102 inserted therein. Inflatable hose 95 therefore inflates and simultaneously tends to relieve the fold therein, and both these effects result in forces which react at the clamp arrangement 90, against the outer surface of limb 83; and against flexible, inelastic strap 100 to create tension in the strap 100. This tension reacts at clamping arrangement 101 to cause anticlockwise rotation of limb 84 and hence output shaft 80. Output shaft 80 can be connected to an artificial limb such as an arm such that the motorized joint of FIGS. 7 and 8 can mimic the action of a human shoulder in one plane of rotation.

Deflation of inflatable hose 95 on selective connection of pipe 97 to a venting arrangement, not shown in FIGS. 7 and 8, but which generally comprises the vent part of a solenoid actuated pneumatic control valve, generally results in reversal of the rotation of the output shaft 80 under the self weight of the limb attached thereto; however, it may be necessary to provide a return spring 502 interconnecting limb 84 and either the framework 82 or fixed limb 83. A suitable type of spring is a tension spring known as a TENSATOR spring.

Alternatively, the motorized joint of FIGS. 7 and 8 can be built in a tandem configuration, having two inflatable elements each selectively connectable to a pressurized air supply to produce rotation of the output shaft in respectively opposite directions.

Strap 100 may be secured to limb 84 to cause clockwise rotation thereof on inflation of the hose 95.

Figure 9:
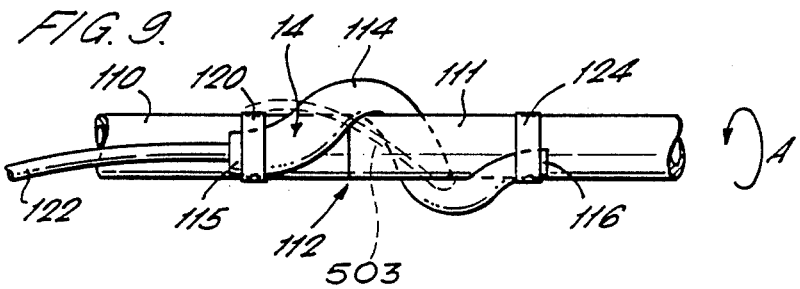
FIG. 9 is a perspective view of a motorized joint comprising a further preferred embodiment of the invention.

A fourth preferred embodiment of the present invention is shown in FIG. 9. The motorized joint of FIG. 9 comprises a pair of circular, hollow skeletal limbs 110, 111 interconnected by a joint 112 permitting relative rotation of limbs 110 and 111 to one another about their common longitudinal axis, while preventing relative movement between the limbs 110 and 111 in the longitudinal axial direction. Bearing arrangements for such joints are well known in the art and generally comprise internally mounted roller bearings to permit relative rotation of the limbs acting in conjunction with two or more internal thrust bearing means to prevent relative axial movement of the limbs.

Interconnecting limbs 110 and 111 is an inflatable element 14 in the form of an inflatable hose 114 having inelastic walls and which is folded in a helical fashion around the outer circumference of circular limbs 110 and 111 to be secured at each end 115, 116 respectively thereof to the limbs 110 and 111. The end 115 of hose 114 is secured to skeletal limb 110 by clamping means 120 as shown in FIGS. 2 and 3. Thus, an air supply and vent pipe 122, which is selectively connectable to either a pressurized air source or a venting arrangement respectively, communicates with the interior of inflatable hose 114. Pipe 122 is retained in position by the clamping means 120 which also seals end 115 of inflatable hose 114 about pipe 122. End 116 of inflatable hose 114 is secured to limb 111 and sealed against escape of air under pressure by clamping means 124. Clamping means 124 is of the type similar to that shown in FIGS. 2 and 3 but which does not incorporate provision for an air supply and vent pipe.

Inflatable hose 114 comprises an elongate sheet (not shown in FIG. 9) of "NETLON" inserted along the interior length thereof to ensure that there is a passage for the flow of air along the hose 114 at all times during the inflation and deflation thereof.

When air supply and vent pipe 122 is connected to a pressurized air supply source (not shown) the inflatable hose 114 inflates and tends to relieve the folding therein. The inflation of hose 114 tends in addition to shorten the distance between the ends 115 and 116 thereof due to the expansion of hose 114 drawing the average center line thereof away from the circumference of the limbs 110 and 111. The effects of expansion of hose 114 and the tendency of said hose to unfold on expansion results in rotation of limb 111 relative to limb 110 in the direction of arrow A in FIG. 9. Deflation of inflatable hose 114, which deflation is caused by selective connection of air supply and vent pipe 122 to a venting arrangement (which in practice is the vent port of a solenoid actuated pneumatic control valve) results in the effects referred to above occurring in an opposite sense to that in which they occur on inflation of inflatable hose 114 and consequently rotation of limb 111 relative to limb 110 in an opposite direction to that indicated by arrow A occurs. If necessary, however, a return spring 503 arrangement may be employed to assist in the operation of the motor driven joint on deflation of the inflatable hose 114. Such a return spring 503 may conveniently be a torsional spring or torsional member, such as a whalebone shaft, interconnecting the interiors of the two hollow, cylindrical, skeletal limbs 110 and 111 to provide a torsional return force.

The embodiment of the invention shown in FIG. 9 may conveniently be used as a wrist joint in artificial limbs, both in models and surgical prostheses; or as a neck joint simulating animal neck movements in animated models. In the latter case, two such joints would be connected in series to provide positive rotational movement of an animal head both to the left and to the right.

Figure 10:
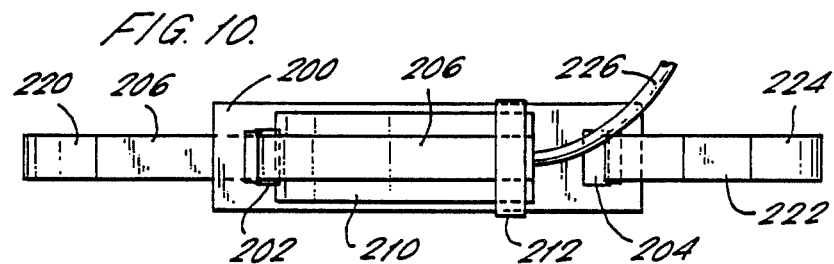
FIGS. 10 and 11 are a top plan view and a longitudinal cross sectional view respectively of a motorized joint comprising a fifth preferred embodiment of the present invention.
Figure 11:
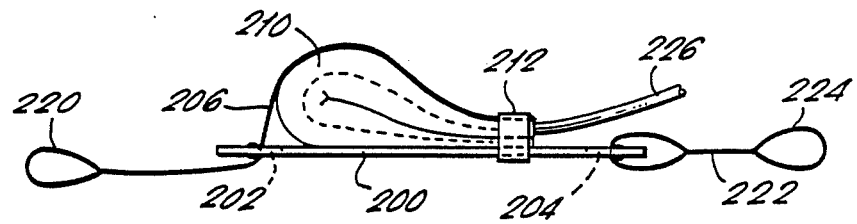

FIGS. 10 and 11 show a fifth preferred embodiment of the present invention. FIG. 10 is a top plan view of a backing plate 200 having transverse slots 202, 204 cut at either end respectively. A flexible, inelastic strap 206 is threaded from the underside of backing plate 200 through slot 202 to pass over the upper surface of folded, inflatable hose 210 which is similarly arranged to that in the embodiment of the invention shown in FIG. 6. Both ends of inflatable hose 210 are clamped by clamping means 212 which is identical with the arrangement shown in FIGS. 4 and 5. One end of strap 206 is secured in clamping means 212 while the other end thereof, which is disposed on the underside of backing plate 200 comprises an eye 220 which, in use, engages a hook disposed on a skeletal limb not shown in FIGS. 10 and 11. Passing through, and secured about slot 204 is a second strap 222 having at the free end thereof a second eye 224 which, in use, engages a hook on a second skeletal limb (not shown). Air supply and vent pipe 226 communicates with the interior of inflatable hose 210 and is selectively connectable to either a pressurized air supply source or a venting arrangement as in embodiments of the invention described hereinabove. In use, inflation of inflatable hose 210 by connection of supply pipe 226, which is sealingly retained in the open end of the inflatable hose by clamping means 212 as shown in FIGS. 4 and 5, to an air supply source, results in expansion and straightening of the hose which, by virtue of forces reacting at clamping means 212 and against backing plate 200, create tension in strap 206. If eye 220 and eye 224 are respectively attached to separate, relatively movable limbs of a motorized joint (not shown in FIGS. 10 and 11) the tension in strap 206 will be transferred via second strap 222 and eyes 220 and 224 to operate the joint in a manner similar to that of the embodiment of the invention shown in FIG. 6. The embodiment of FIGS. 10 and 11 is therefore an embodiment of the invention which can be installed temporarily in a joint and subsequently removed without necessitating complete dismantling of the joint.

Figure 12:
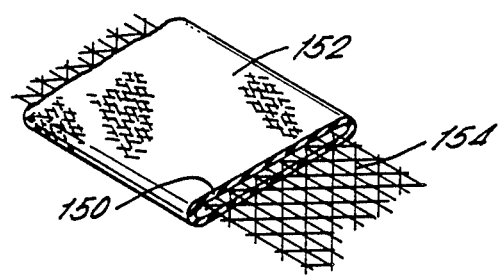
FIG. 12 is a perspective view of a length of inflatable hose for use in the embodiments of the invention described herein.

FIG. 12 is a representation of a length of the inflatable hose used to form the inflatable element of all the embodiments of the invention described above. The hose comprises an inner neoprene tube 150 covered with and bonded to a fibrous webbing sheath 152. It will be clear from FIG. 12 that the hose, when deflated, is of generally flat transverse cross-section. The hose, however, will tend to adopt a circular cross-section on inflation and this arrangement allows a significant force due to expansion to be obtained from an essentially inextensible hose.

A flexible, flat sheet 154 of nylon mesh netting, such as "NETLON" is inserted within the hose and serves to maintain a passage for the flow of air or other fluid through the hose no matter how severely folded or kinked the hose may become. This effect is achieved by the opposing interior faces of the neoprene tube 150 being prevented at all times from meeting fully and hence sealing the pipe in the vicinity of a strand of the mesh.

Clearly, any filament-like feature preventing full closure of the neoprene tube 150 would have a similar effect to that of the nylon mesh. Examples of such filament-like features include raised contours moulded on the interior faces of the neoprene tube, or lengths of nylon twine or similar material inserted into the tube. However, the use of a flexible mesh has significant advantages over such alternative methods since a sheet of nylon mesh, of appropriate dimensions, is generally self-centering in the neoprene tube; and further the cost of a mesh such as "NETLON" is low while maintaining adequate durability.

Figure 13:
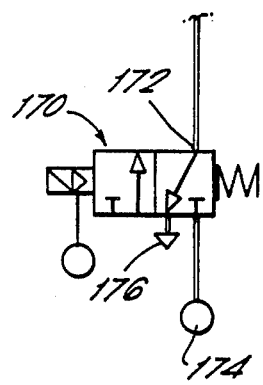
FIGS. 13 to 15 are schematic views of hydraulic or pneumatic circuits comprising motorized joints each according to the present invention.
Figure 14:
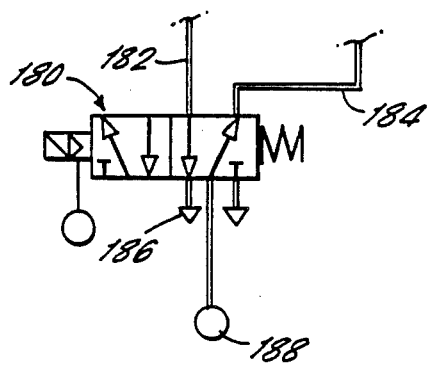
Figure 15:
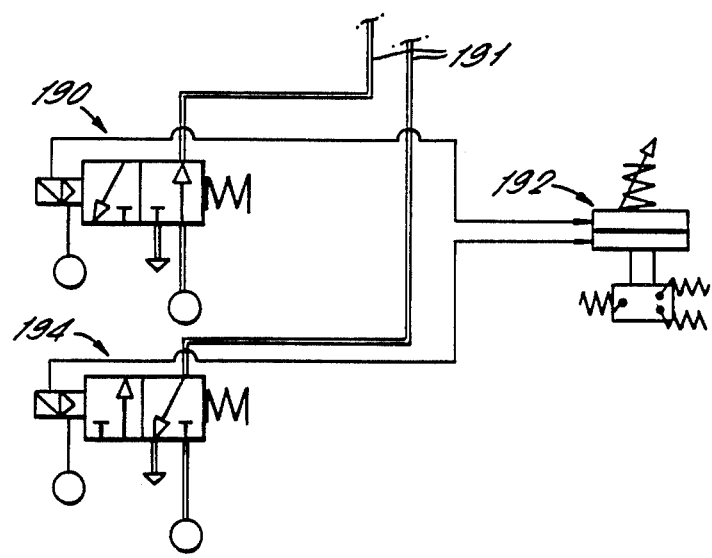

FIGS. 13 to 15 inclusive of the drawings are schematic representations of simple pneumatic or hydraulic arrangements which may be used as part of a control circuit for motorized joints of the kinds described hereinabove.

FIG. 13 shows a simple 3-port 2-position solenoid actuated valve 170, which valves are well known in the art, and which may have the supply port 172 thereof selectively connected to either a pneumatic or hydraulic main 174 or a vent port 176 by virtue of the position of the solenoid actuator. The output supply port 172 is connected to an air supply and vent pipe of a motorized joint according to the invention and through which the inflatable element may be either inflated or deflated as desired.

FIG. 14 shows a 5-port, 2-position solenoid actuated valve 180, which is used similarly to the valve of FIG. 13 for controlling a pair of motorized joints according to the present invention. The joints are respectively connected to an air supply 188, according to the position of valve 180, by respective pipes 182 and 184. When one of the joints is connected to air supply 188, the other is connected to a vent port 186, and vice versa. The pair of motorized joints may be arranged in a configuration permitting opposed operation of the joints using the valve of FIG. 14.

FIG. 15 shows a simple proportional control circuit comprising a pair 190, 194 of 3-port, 2-position solenoid actuated valves arranged to operate with a pressure switch 192 to provide proportional inflation and venting of the inflatable members via pipes 191 according to the setting of pressure switch 192.

It will be appreciated that all the pneumatic circuits referred to hereinabove can equally well be arranged to operate with a hydraulic working fluid.

The embodiments described hereinabove represent the essential features of artificial limbs to be constructed in accordance with the invention. It will be clear that, for complete realism of appearance and movement of limbs so constructed, the motorized joints described above are covered in some material resembling human or animal flesh, skin and where necessary, fur. When so covered, the motorized joints of the invention have an extremely realistic appearance since, in use, movement of the motorized joint results in an apparent flexing or tensing of the artificial muscle comprised within the joint. This feature, coupled with those of low internal friction referred to above, creates a wholly convincing appearance and action in the artificial limbs comprising motorized joints of the present invention. Suitable materials for covering the motorized joints include a number of proprietary and specialized foamed rubbers and plastics, along with semi-elastic plastic outer coverings to represent animal or human skin A wide variety of physical features of appearance can therefore be incorporated within the limb, adding to the effects of realism created therein. Such features have many advantages, both in producing lifelike models for high-technology television and film recordings, and in alleviating many of the psychological disadvantages suffered by some recipients of artificial limb prostheses.

Finally, it will be clear that the applications of the motorized joint of the present invention extend beyond those described above. There are many instances in the field of industrial robotics, for example, where it is advantageous to have a robot arm capable of moving in a number of non-parallel planes using motors having very low internal friction, with the motors also being highly amenable to proportional control. Such robot arms can easily be constructed, at very low relative cost, using the principles of the invention described herein.

We claim:

1. A motorized joint comprising a pair of relatively movable members; an elongate, inflatable element having an inextensible wall; means for holding apart opposing inner surfaces of the inflatable element such that a fluid passage exists within the inflatable element; actuating means having means for inflating the inflatable element causing it to increase in cross section; and means mounting the two ends of said inflatable element in a folded condition on one of the relatively movable members and acting on the other relatively movable member whereby inflation of the inflatable element causes relative movement between the relatively movable members.

2. A motorized joint according to claim 1 wherein the relatively movable members are mounted for relative rotation about parallel axes, and further including means for transmitting a force resulting from inflation of the inflatable element to the other relatively movable member to effect relative rotation of the relatively movable members.

3. A motorized joint according to claim 2, wherein the relatively movable members are mounted in a framework interconnecting each other and permitting relative rotation therebetween.

4. A motorized joint according to claim 1 wherein the inflatable element comprises a length of inflatable, hollow hose sealed at one end and unsealed at the other end and having a generally flat transverse cross section when in a deflated state.

5. A motorized joint according to claim 4 wherein the means to inflate the inflatable element comprises means to supply fluid under pressure to the interior of said inflatable element, said supply fluid means including a fluid supply pipe retained in an aperture at the unsealed end of the inflatable element; at least one sealing block means adapted to seal said unsealed end of the inflatable element having the fluid supply pipe retained therein; clamping means to press said sealing block means into contact with said ends of the inflatable element against a reaction surface also adapted to accommodate said ends of the inflatable element; pressurized fluid supply means selectively connectable to said supply pipe to supply inflating fluid thereto; and venting means selectively connectable to said supply pipe for use in deflating said inflatable element.

6. A motorized joint according to claim 1 further comprising means for securing the inflatable element to at least one of said relatively movable members, said means for securing including clamping means for securing the inflatable element to at least one of said relatively movable member.

7. A motorized joint according to claim 1 wherein the means for holding apart opposing inner surfaces of the inflatable element comprises a length of flat, flexible, moulded plastic netting of narrow width than the narrowest transverse dimension of the inflatable element when inflated, said length of netting being inserted lengthwise in said inflatable element to maintain separation of opposing inner surfaces of the inflatable element on collapsing of said inflatable element on deflation, folding and kinking thereof.

8. A motorized joint according to claim 1 further comprising spring means interconnecting the relatively movable members, said spring means, on deflation of the inflatable element, causes reversal of the movement between the relatively movable members.

9. A motorized joint according to claim 1 further comprising a pneumatic circuit arranged to control inflation and deflation of the inflatable element.

10. A motorized joint according to claim 1 further comprising an hydraulic circuit arranged to control inflation and deflation of the inflatable element.

* * * * *

UNITED STATES PATENT AND TRADEMARK OFFICE
CERTIFICATE OF CORRECTION

PATENT NO. : 4,944,755

DATED : July 31, 1990

INVENTOR(S) : James R. Hennequin, et al.

It is certified that error appears in the above-identified patent and that said Letters Patent is hereby corrected as shown below:

On the title page, Attorney, Agent or Firm, change "Tabin, Flannery" to --Tabin & Flannery--; and after the ABSTRACT, change "10 Claims" to --11 Claims--.

change "Tabin, Flannery" to --Tabin & Flannery--.

Column 14, line 43, change "causes" to --causing--.

Column 14, line 29, change "member" to --members--.

Column 14, line 33, change "narrow" to --narrower--.

Column 14, line 51, add the following claim:

--11. A motorized joint according to claim 1 further comprising a hinged joint interconnecting the relatively movable members.--

Signed and Sealed this

Thirtieth Day of June, 1992

Attest:

DOUGLAS B. COMER

*Attesting Officer*     *Acting Commissioner of Patents and Trademarks*